US008524273B2

(12) United States Patent
Amano et al.

(10) Patent No.: US 8,524,273 B2
(45) Date of Patent: Sep. 3, 2013

(54) TRANSDERMAL ABSORPTION PREPARATION

(75) Inventors: Satoshi Amano, Ibaraki (JP); Sachiko Honma, Ibaraki (JP); Tetsuro Tateishi, Ibaraki (JP); Natsumi Kase, Ibaraki (JP)

(73) Assignee: Hisamitsu Pharmaceutical Co., Inc., Saga (JP)

( * ) Notice: Subject to any disclaimer, the term of this patent is extended or adjusted under 35 U.S.C. 154(b) by 932 days.

(21) Appl. No.: 12/224,586

(22) PCT Filed: Feb. 27, 2007

(86) PCT No.: PCT/JP2007/053671
§ 371 (c)(1),
(2), (4) Date: Aug. 28, 2008

(87) PCT Pub. No.: WO2007/099966
PCT Pub. Date: Sep. 7, 2007

(65) Prior Publication Data
US 2009/0068252 A1 Mar. 12, 2009

(30) Foreign Application Priority Data
Feb. 28, 2006 (JP) ................................ 2006-052370

(51) Int. Cl.
*A61K 47/32* (2006.01)
*A61K 9/70* (2006.01)
*A61K 9/14* (2006.01)
*A61K 31/135* (2006.01)
*A61F 13/02* (2006.01)

(52) U.S. Cl.
USPC ........... 424/449; 424/448; 424/487; 514/652; 514/772.4

(58) Field of Classification Search
USPC .............. 424/449, 448, 487; 514/652, 772.4, 514/487
See application file for complete search history.

(56) References Cited

U.S. PATENT DOCUMENTS

| 4,889,721 | A | 12/1989 | Ueda et al. |
| 5,656,286 | A * | 8/1997 | Miranda et al. ............... 424/449 |
| 6,074,665 | A | 6/2000 | Horstmann et al. |
| 6,689,379 | B1 * | 2/2004 | Bracht .......................... 424/448 |
| 7,279,178 | B1 | 10/2007 | Berthold |
| 2003/0228354 | A1 | 12/2003 | Muraoka et al. |
| 2004/0096491 | A1 | 5/2004 | Tateishi et al. |
| 2005/0136101 | A1 | 6/2005 | Berthold |
| 2006/0240086 | A1 | 10/2006 | Tateishi et al. |

FOREIGN PATENT DOCUMENTS

| EP | 1 197 209 A1 | 4/2002 |
| EP | 1 541 177 A1 | 6/2005 |
| EP | 1 591 110 A1 | 11/2005 |
| JP | 63-203616 | 8/1988 |
| JP | 1-104008 | 4/1989 |
| JP | 05-271056 | 10/1993 |
| JP | 06-205839 | 7/1994 |
| JP | 11-512080 T | 10/1999 |
| JP | 2003-507417 T | 2/2003 |
| JP | 2003-104875 | 4/2003 |
| JP | 2003104875 A * | 4/2003 |
| JP | 2003-313122 | 11/2003 |
| JP | 2004-010525 | 1/2004 |
| WO | WO-02/069942 A1 | 9/2002 |
| WO | WO-2005/011662 | 2/2005 |

OTHER PUBLICATIONS

Modamio et al., 1998, International Journal of Pharmacuetics, 173, 141-148.*

* cited by examiner

*Primary Examiner* — Abigail Fisher
(74) *Attorney, Agent, or Firm* — Edwards Wildman Palmer LLP; Peter F. Corless; Christine C. O'Day (57) ABSTRACT

A transdermal absorption preparation having a support and a pressure-sensitive adhesive layer consisting of multiple layers, wherein the pressure-sensitive adhesive layer comprises a drug-retaining layer containing a drug and an acrylic pressure-sensitive adhesive and a skin adhesion layer containing a styrene-isoprene-styrene block copolymer. This preparation can continuously release bisoprolol at a constant concentration. Moreover, it can be easily produced.

10 Claims, 2 Drawing Sheets

TRANSDERMAL ABSORPTION PREPARATION

TECHNICAL FIELD

The present invention relates to a transdermal absorption preparation (transdermal patch) which delivers a predetermined amount of drug continuously through skin or mucosa.

BACKGROUND ART

In order to obtain a drug action, there are two means, in which the drug is administered orally, or administered transdermally. Transdermal administration has a number of advantages over oral administration. For example, in oral administration method of drug, the drug absorbed from intestine is first metabolized at liver before it presents its action at a desired place, and a large amount thereof is degraded, whereas transdermal administration method has an advantage that the absorbed drug does not pass liver first when circulating in the body, so that its drug action is not decreased severely by the metabolism at liver.

Further, transdermal administration method has another advantage that it provides a continued drug effect, and it has a constant drug release property.

For example, the drug of the general formula (1)

(1)

wherein R is 2-isopropoxyethoxymethyl group (bisoprolol), carbamoylmethyl group (atenolol) or 2-methoxyethyl group (metoprolol), is a β-blocker and a therapeutic drug of essential hypertension that selectively blocks $\beta_1$ receptor of sympathetic nervous system, and does not have intrinsic sympathetic nervous stimulating action.

Although the above therapeutic drugs are only used as oral drugs in the clinical site at present, bisoprolol (R: 2-isopropoxyethoxymethyl group), among the drugs represented by general formula (1), in particular, has relatively little effects on bronchi due to the high $\beta_1$ selectivity. However, when bisoprolol is administered orally, symptoms such as bradycardia, dizziness and feeling of weariness may occur, and from the view point of stabilization of drug levels in the blood and a continuous drug effect, development of a preparation for transdermal administration in the form of adhesive patch and the like rather than the one for oral administration is desired.

Taking such a state into consideration, as a transdermal patch controlling the release property of the drug, it has been proposed to control it by making the adhesive base in laminated form (Patent document 1 and Patent document 2). Patent document 1 describes a laminate-type transdermal patch wherein a fine powder such as of titanium oxide, silica and aluminum silicate together with a drug in an adhesive layer that does not contact with skin. However, this preparation has the problems that the fine powder may be involved in various reactions such as degradation of drug and base, and that physical property necessary for the adhesive agent such as adherability and cohesiveness is impaired.

Further, Patent document 2 describes that a predetermined amount of a drug is absorbed transdermally continuously by laminating an adhesive layer of natural rubber, synthetic rubber, acrylic resin and the like having a similar solubility parameter to that of the drug. However, this laminate-type adhesive agent has the problems that the drug is prone to move between laminates, and in the actual use, the drug cannot be released in a controlled manner, because it is necessary to laminate the adhesive agent layer with a similar property so that every adhesive layer to be laminated can comprise a high concentration of a drug, and it has also the problem that the availability of the drug is low and the cost of production increases because the adhesive agent with a high solubility of a drug is used. Moreover, it has the problem that adhesive properties are deteriorated by the drug concentration that is higher than the saturation concentration.

Further, embodiments for controlling the releasing property of bisoprolol are disclosed for example in Patent documents 3 to 5. In Patent document 3, the art of preventing a decrease of cohesion caused by sweating from the skin using acryl/acryl laminate is disclosed, but in the viewpoint of controlling drug release, because acryl/acryl laminate has very similar chemical properties between layers, it had the problem that the drug is prone to move between layers, and in the case of practical use, it cannot provide the drug in a sustained manner.

Further, Patent document 4 discloses that the laminate of rubber/fluorine-containing polymer prevents the recrystallization of the drug by providing a layer with lower diffusion rate to the skin side, and Patent document 5 discloses that the laminate of high-molecular-weight polymer/amorphous prevents cold flow of the adhesive patch by utilizing the difference in glass transition point. However, these known prior arts do not describe the drug release property at all, and had the problem that the production process is complicated because a large number of layers are laminated.

[Patent document 1] JP, A, 5-271056
[Patent document 2] JP, A, 6-205839
[Patent document 3] JP, A, 2004-10525
[Patent document 4] JP, A, 11-512080
[Patent document 5] JP, A, 2003-507417

DISCLOSURE OF INVENTION

Problems to be Solved by the Invention

That is, the problem to be solved by the present invention is to provide a transdermal patch that can release a drug in a sustained manner and at a constant concentration from the preparation, and in addition the production process thereof is easy.

Means for Solving the Problems

The present inventors have researched intensively so as to solve the above problem, and as a result, have found that a preparation having at least a drug reservoir layer comprising an acrylic pressure-sensitive adhesive on the backing-side, and a skin adhesion layer containing a styrene-isoprene-styrene block copolymer on the skin contact side, can control the drug releasing property effectively, and the production process thereof is simple, and thus completed the present invention.

That is, the present invention relates to a transdermal patch comprising a backing and a pressure-sensitive adhesive layer which comprises multiple layers, wherein the pressure-sensitive adhesive layer comprises a drug reservoir layer containing a drug and an acrylic pressure-sensitive adhesive, and a skin adhesion layer containing a styrene-isoprene-styrene block copolymer.

Further, the present invention relates to the transdermal patch, wherein the drug is represented by the general formula (1)

$$\text{(CH}_3\text{)}_2\text{CH-NH-CH}_2\text{-CH(OH)-CH}_2\text{-O-C}_6\text{H}_4\text{-R} \quad (1)$$

wherein

R is one selected from the group consisting of 2-isopropoxyethoxymethyl, carbamoylmethyl, and 2-methoxyethyl groups.

In addition, the present invention relates to the transdermal patch, wherein R is a 2-isopropoxyethoxymethyl group.

Further, the present invention relates to the transdermal patch, wherein the acrylic pressure-sensitive adhesive is a copolymer comprising (meth)acrylic acid having a carboxyl group as a monomer unit.

In addition, the present invention relates to the transdermal patch, wherein the acrylic pressure-sensitive adhesive is a copolymer comprising 2-ethylhexyl acrylate as a monomer unit.

Further, the present invention relates to the transdermal patch, characterized in that the drug reservoir layer further comprises a solubilizer and/or a permeation enhancer.

In addition, the present invention relates to the transdermal patch, characterized in that the skin adhesion layer further comprises one or more selected from the group consisting of a synthetic rubber, a tackifier resin, and a plasticizer.

Further, the present invention relates to the transdermal patch, characterized in that the synthetic rubber is one or more selected from the group consisting of polyisobutylene, isoprene rubber, styrene-butadiene-styrene copolymer, and styrene-butadiene rubber.

In addition, the present invention relates to the transdermal patch, characterized in that the content of the drug or a pharmaceutically acceptable salt thereof is 10 to 60% by mass.

Effects of the Invention

The transdermal patch of the present invention can easily be produced, allows for transdermal absorption of the drug for a long time in a sustained manner at a stable skin permeation rate, and has an excellent adherence to the skin, so that it is extremely useful for the treatment of a wide range of diseases, in particular of hypertension.

BEST MODE FOR CARRYING OUT THE INVENTION

The transdermal patch of the present invention is an adhesive patch comprising a backing layer and a pressure-sensitive adhesive layer. The pressure-sensitive adhesive layer is further divided into two or more layers, a skin adhesion layer exists as the layer for adhering to skin which is the farthest from the backing, and a drug reservoir layer exists between the backing and the skin adhesion layer. Further, the preparation comprises a detachable sheet which covers the side of the skin adhesion layer contacting with skin and is removed prior to use, in order to protect the skin-adhesion part of the present adhesive patch until use.

The backing of the transdermal patch of the present invention is not expressly limited as long as it can hold a pressure-sensitive adhesive layer, and a stretch or non-stretch backing can be used. For example, it is selected from woven cloth, textile, non-woven cloth, polyurethane, polyester, polyvinyl acetate, polyvinylidene chloride, polyethylene, polyethylene terephthalate, aluminum sheet, and the like, or a composite material thereof, or a laminate thereof.

In particular, the stretch or non-stretch sheet consisting of polyethylene terephthalate is preferred.

The drug reservoir layer in the transdermal patch of the present invention is not expressly limited as long as it is an acrylic pressure-sensitive adhesive and can retain a drug, whereas (meth)acrylic polymer which can retain a drug with high polarity such as bisoprolol in a large amount and stably is preferably used.

Further, as to (meth)acrylic polymer, it is not expressly limited as long as it is co-polymerized with comprising at least one of (meth)acrylic esters typified by 2-ethylhexyl acrylate, methyl acrylate, butyl acrylate, hydroxyethyl acrylate, 2-ethylhexyl methacrylate and the like, for example, acrylic acid/octyl acrylate copolymer, 2-ethylhexyl acrylate/N-vinyl-2-pyrrolidone/1,6-hexane glycol dimethacrylate copolymer, 2-ethylhexyl acrylate/vinyl acetate copolymer, 2-ethylhexyl acrylate/vinyl acetate/acrylic acid copolymer, 2-ethylhexyl acrylate/butyl acrylate/acrylic acid copolymer, 2-ethylhexyl acrylate/methyl acrylate/glycidyl methacrylate/acrylic acid copolymer, 2-ethylhexyl acrylate/2-ethylhexyl methacrylate/dodecyl methacrylate copolymer, methyl acrylate/2-ethylhexyl acrylate co-polymerized resin emulsion, an adhesive such as acrylic polymer comprised in acrylic resin alkanolamine solution, Duro-Tak® acrylic adhesive series (manufactured by National Starch and Chemicals Co.), GELVA acrylic adhesive series (manufactured by Monsanto Co.), SK-Dyne Matriderm (Soken Chemical & Engineering Co., Ltd.), Eudragit® series (HIGUCHI INC.) and the like can be used. Further, as to the (meth)acrylic ester at least one of which is comprised in and co-polymerized with (meth)acrylic polymer, 2-ethylhexyl acrylate is preferred.

Further, among the above (meth)acrylic polymers, a (meth)acrylic polymer having a carboxyl group is preferably used, taking the stability of the drug such as bisoprolol or a salt thereof into consideration. Such (meth)acrylic polymers are not limited expressly as long as they have substantially no hydroxyl group and have a carboxyl group, and include, for example, 2-ethylhexyl acrylate/vinyl acetate/acrylic acid copolymer, 2-ethylhexyl acrylate/butyl acrylate/acrylic acid copolymer, 2-ethylhexyl acrylate/methyl acrylate/glycidyl methacrylate/acrylic acid copolymer, Duro-Tak® 87-2100, Duro-Tak® 87-2852, Duro-Tak® 87-2194, Duro-Tak®87-2196, Duro-Tak® 87-2353, Duro-Tak® 87-2051, Duro-Tak® 87-2052, Duro-Tak® 87-2054, Duro-Tak® 87-2825, Duro-Tak® 87-2677 (manufactured by National Starch and Chemicals Co.), and the like.

The drug reservoir layer using such a carboxyl group-containing acrylic polymer can contain a drug such as bisoprolol in a high concentration and stably.

The content of the acrylic pressure-sensitive adhesive in the drug reservoir layer is, usually, in the range of 10 to 60% by mass, preferably 20 to 50% by mass, particularly preferably 30 to 40% by mass. A content of less than 10% is not preferable because sufficient skin permeability cannot be obtained, whereas a content of more than 60% is not preferable because a sufficient cohesion as an adhesive patch cannot be maintained.

The drugs used in the transdermal patch of the present invention include, but not limited to hypnotic/sedative agent, antipyretic antiinflammatory agent, steroidal anti-inflammatory drug, analeptic/stimulant, neuropsychiatric drug, hormone preparation, local anesthetic, agent for urinary tract, skeletal muscle relaxant, agent for genital organ, antiepileptic drug, agent for autonomic nerve, antiparkinsonian agent, diuretic, respiratory stimulant, antimigraine agent, antihistamine, bronchodilator, cardiotonic, coronary vasodilator, peripheral vasodilator, stop smoking aid, antihypertensive, agent for arrhythmia, anti-malignant ulcer agent, lipid-lowering agent, hypoglycemic, anti-gastrointestinal ulcer drug, cholagogue, gastrointestinal prokinetic agent, agent for liver disease, anti-allergic agent, antiviral agent, antibiotic, agent for habitual intoxication, appetite suppressant, chemotherapeutic agent, blood coagulation accelerator, anti-Alzheimer agent, serotonin receptor antagonist antiemetic, antigout drug, narcotic analgesic, and the like.

As to the transdermal patch of the present invention, among the above drugs, antihypertensives ($\alpha$-blocker, $\beta$-blocker, Ca antagonist, ACE inhibitor, angiotensin II receptor blocker) are preferable, in particular, $\beta$-blocker is preferable, and among others bisoprolol is the most preferable. Further, the drugs are used as a free base or a pharmacologically acceptable salt.

Pharmacologically acceptable salts include, for example, hydrochloride, hydrobromide, nitrate, sulfate, phosphate, formate, acetate, trifluoroacetate, propionate, lactate, tartrate, oxalate, fumarate, maleate, citrate, malonate, methanesulfonate and the like.

The content of the drug formulated into the drug reservoir layer is usually in the range of 10 to 60% by mass, preferably 20 to 50% by mass, particularly preferably 30 to 40% by mass. The drug may be contained in the drug reservoir layer in a dissolved state, supersaturated crystalline state or a dispersed state.

A content of less than 10% by mass may not be preferable because sufficient skin permeability cannot be obtained, while a content of more than 60% by mass may not be preferable because a sufficient cohesion as an adhesive patch cannot be maintained. The drug reservoir layer of the present transdermal patch comprises an acrylic adhesive constituent with high polarity, so that a drug such as bisoprolol with high polarity or pharmaceutically acceptable salts thereof can be retained in a large amount and stably.

The drug reservoir layer of the transdermal patch of the present invention may further contain a solubilizer and/or a permeation enhancer. As to the solubilizer, any type of compounds capable to dissolve the drug may be used. Further, as to the permeation enhancer, any compound previously known to have absorption promotion action to the skin may be used.

As to solubilizer and/or permeation enhancer, illustrative are, for example, fatty acids with carbon chain number of 6 to 20, fatty alcohols, fatty acid esters, amides or ethers, aromatic organic acids, aromatic alcohols, aromatic organic acid esters or ethers (these may be saturated or unsaturated, and may be cyclic, straight or branched), furthermore lactic acid esters, acetic acid esters, monoterpene compounds, sesquiterpene compounds, Azone, Azone derivatives, pirotiodecane, glycerol fatty acid esters, propylene glycol fatty acid esters, sorbitan fatty acid esters (Span type), polysorbates (Tween type), polyethylene glycol fatty acid esters, polyoxyethylene hydrogenated castor oils (HCO type), polyoxyethylene alkyl ethers, sucrose fatty acid esters, plant oils and the like.

Specifically, caprylic acid, capric acid, caproic acid, lauric acid, myristic acid, palmitic acid, stearic acid, isostearic acid, oleic acid, linoleic acid, linolenic acid, lauryl alcohol, myristyl alcohol, oleyl alcohol, isostearyl alcohol, cetyl alcohol, methy laurate, hexyl laurate, diethyl sebacate, lauric diethanolamide, isopropyl myristate, myristyl myristate, octyldodecyl myristate, isopropyl palmitate, cetyl palmitate, salicylic acid, methyl salicylate, ethylene glycol salicylate, cinnamic acid, methyl cinnamate, cresol, cetyl lactate, lauryl lactate, ethyl acetate, propyl acetate, geraniol, thymol, eugenol, terpineol, 1-menthol, borneol, d-limonene, isoeugenol, isoborneol, nerol, dl-camphor, glycerol monocaprylate, glycerol monocaprate, glycerol monolaurate, glycerol monooleate, sorbitan monolaurate, sucrose monolaurate, polysorbate 20, propylene glycol, propylene glycol monolaurate, polyethylene glycol monolaurate, polyethylene glycol monostearate, polyoxyethylene lauryl ether, HCO-60, pyrothiodecane and olive oil are preferable, and lauryl alcohol, myristyl alcohol, oleyl alcohol, isostearyl alcohol, diethyl sebacate, glycerol monocaprate, glycerol monolaurate, glycerol monooleate, sorbitan monolaurate, propylene glycol monolaurate, polyoxyethylene lauryl ether and pyrothiodecane are particularly preferable, and isopropyl myristate is more preferable.

Each of these solubilizers and permeation enhancer may be used alone, or two or more may be used in combination. The content thereof is not limited expressly, whereas 1 to 40% by mass is preferable, 1 to 20% by mass is more preferable, and 1 to 10% by mass is particularly preferable, based on the total amount of the compounds contained in the drug reservoir layer.

The pressure-sensitive adhesive layer of the transdermal patch of the present invention has a skin adhesion layer for the contact with skin, which is laminated on an acrylic drug reservoir layer, and the transdermal patch of the present invention may further be provided with a plurality of layers between the drug reservoir layer and the skin adhesion layer, as long as the object of the present invention is accomplished.

The base agent of the skin adhesion layer includes a rubber-type adhesive constituent. As to the rubber-type adhesive constituent, a styrene-isoprene-styrene block copolymer is particularly preferably used.

According to the present invention, the acrylic adhesive constituent used for the drug reservoir layer consists of monomer constituents which have functional groups such as hydroxyl, carboxyl, or ester group and the like, and has a high polarity, whereas since the rubber-type adhesive constituent consists of monomer constituents which do not have such functional groups, it has a low polarity, and thus physical-chemical properties are very different. In case that bisoprolol is used as a drug in the present invention, it becomes possible to effectively control the transfer of bisoprolol having a high polarity from the drug reservoir layer to the skin adhesion layer by laminating the acrylic drug reservoir layer with the pressure-sensitive adhesive layer of the rubber-type adhesive constituent, so that bisoprolol can be absorbed transdermally for a long time in a sustained manner and stably.

The content of the styrene-isoprene-styrene block copolymer in the skin adhesion layer is preferably 5 to 30% by mass, because, when the content is less than 5% by mass, there is a tendency that sufficient permeability and cohesion as an adhesive patch cannot be maintained, whereas when the content is more than 30% by mass, sufficient adhesivity as an adhesive patch cannot be maintained The skin adhesion layer of the transdermal patch of the present invention may further comprise synthetic rubbers in addition to the above-mentioned styrene-isoprene-styrene block copolymer, and as to the synthetic rubbers, polyisobutylene, isoprene rubber, styrene-butadiene-styrene copolymer, styrene-butadiene rubber, polysiloxane, and the like can preferably be used. Each of these synthetic rubbers may be used alone, or two or more may be used in combination. Among these, polyisobutylene is especially preferable, and it is more preferable that two or more polyisobutylenes having different molecular weights are used in combination. As to the content of the synthetic rubbers, 1 to 30% by mass is preferable, and 5 to 20% by mass is more preferable.

Also, in case that styrene-isoprene-styrene block copolymer (SIS) and polyisobutylene (PIB) are used for the skin adhesion layer of the transdermal patch of the present invention, the adherence to skin can be varied arbitrarily by varying the composition ratio thereof. For example, if the content of the styrene-isoprene-styrene block copolymer is increased, the adhesion force can be diminished, and conversely, if the content of the polyisobutylene is increased, the adhesion force can be increased. The preferable content of SIS and PIB for maintaining an adhesivity so that the preparation can adhere for a long period, and for preventing that a residue of pressure-sensitive adhesive is remained on skin when removing, is SIS/PIB=70/30 to 40/60, more preferably SIS/PIB=50/50 to 40/60.

Further, a tackifier resin may desirably be contained in the skin adhesion layer of the present invention in case that the adhesivity is not sufficient to continue the application for at least 12 hours, and as usable tackifier resins, illustrative are rosin derivatives (e.g., rosin, glycerol esters of rosin, hydrogenated rosin, glycerol esters of hydrogenated rosin, pentaerythritol esters of rosin and the like), alicyclic saturated hydrocarbon resins (e.g., Arkon™ P-100, Arakawa Chemical Industries, Ltd.), aliphatic hydrocarbon resins (e.g., Quintone® B170, Zeon Coorporation), terpene resins (e.g., Clearon™ P-125, Yasuhara Chemical, Co., Ltd.), maleic acid resins and the like. In particular, glycerol esters of hydrogenated rosin, alicyclic saturated hydrocarbon resins and terpene resins are preferable.

One of these tackifying agents may be used alone, or two or more may be used in combination. The content is not limited expressly, whereas 10 to 60% by mass is preferable, 20 to 60% by mass is more preferable, and 30 to 50% by mass is particularly preferable.

In addition, a plasticizer may be contained in the skin adhesion layer of the transdermal patch of the present invention. As plasticizers, illustrative are petroleum oils (e.g., paraffinic process oil, naphthenic process oil, aromatic process oil and the like), squalane, squalene, vegetable oils (e.g., olive oil, camellia oil, castor oil, tall oil, peanut oil), silicone oil, dibasic acid esters (e.g., dibutyl phthalate, dioctyl phthalate and the like), liquid rubber (e.g., polybutene, liquid isoprene rubber), liquid fatty acid esters (isopropyl myristate, hexyl laurate, diethyl sebacate, diisopropyl sebacate), diethylene glycol, polyethylene glycol, glycol salicylate, propylene glycol, dipropylene glycol, triacetin, triethyl citrate, crotamiton and the like. In particular, liquid paraffin, liquid polybutene, isopropyl myristate, diethyl sebacate and hexyl laurate are preferable.

One of these plasticizers may be used alone, or two or more may be used in combination. The content of these plasticizers is not limited expressly, whereas 5 to 50% by mass is prefer-able, 10 to 40% by mass is more preferable, and 20 to 30% by mass is particularly preferable, in the skin adhesion layer.

In addition, in the present invention, as required, antioxidants, fillers, cross-linking agents, preservatives or UV absorbers and the like can be blended in the drug reservoir layer and the skin adhesion layer.

As antioxidants, tocopherol and its ester derivatives, ascorbic acid, ascorbyl stearate, nordihydroguaiaretic acid, dibutyl hydroxy toluene (BHT), butyl hydroxy anisole are preferable; as fillers, calcium carbonate, magnesium carbonate, silicate (e.g., aluminum silicate, magnesium silicate, bentonite, kaolin and the like), silicic acid, barium sulfate, calcium sulfate, calcium zincate, zinc oxide, titanic oxide are preferable; as cross-linking agents, thermosetting resins such as amino resins, phenol resins, epoxy resins, alkyd resins and unsaturated polyesters, isocyanate compounds, block isocyanate compounds, organic cross-linking agents, and inorganic cross-linking agents such as metals or metal compounds, are desirable. Further, as preservatives, ethyl p-hydroxy benzoate, propyl p-hydroxy benzoate, butyl p-hydroxy benzoate are preferable; as UV absorbers, p-amino benzoic acid derivatives, anthranilic acid derivatives, salicylic acid derivatives, coumarin derivatives, amino-acid compounds, imidazoline derivatives, pyrimidine derivatives, dioxane derivatives are preferable.

The content of each of the above antioxidants, fillers, cross-linking agents, preservatives, UV absorbers is not limited expressly, whereas the total amount of antioxidants, fillers, cross-linking agents, preservatives and UV absorbers is preferably 0.01 to 20% by mass, more preferably 0.1 to 10% by mass, and particularly preferably 0.1 to 5% by mass, based on the total amount of the constituents contained in each of the drug reservoir layer and the skin adhesion layer, the amount being calculated separately for each layer.

Also, the transdermal patch of the present invention can be provided with further layers, such as acrylic pressure-sensitive adhesive, rubber type pressure-sensitive adhesive and release controlling membrane between the drug reservoir layer and the skin adhesion layer. In addition, the transdermal patch of the present invention can be provided with further layers, such as acrylic pressure-sensitive adhesive, rubber pressure-sensitive adhesive, and release controlling membrane between the backing and the drug reservoir layer.

The pressure-sensitive adhesive layer of the adhesive patch of the present invention is provided with detachable sheet on the side contacting with skin, opposite to the backing. As detachable sheet, illustrative are, e.g., film such as of polyesters such as polyethylene terephthalate, polyvinyl chloride and polyvinylidene chloride, a laminated film of a high-quality paper with polyolefin. These detachable sheets are preferably siliconized on the surface of the side contacting with the pressure-sensitive adhesive layer. Siliconization makes it possible for the detachable sheet to be detached from the pressure-sensitive adhesive layer easily at the time of use.

The process for producing the transdermal patch of the present invention is not limited expressly, whereas, as one embodiment thereof, for example, it can be produced by dissolving an acrylic pressure-sensitive adhesive and a drug in an organic solvent such as ethyl acetate, and after applying the obtained solution onto a release film and drying, adhering a backing to a drug reservoir layer to form a drug reservoir layer, on the other hand, applying onto a release liner a solution of a styrene-isoprene-styrene block copolymer, a synthetic rubber, a tackifier resin, and a plasticizer in an organic solvent, drying, detaching the release film from the drug reservoir layer obtained earlier, and laminating the pressure-sensitive adhesives together.

The drug-containing laminated adhesive patch having the configuration of the exemplary embodiment of the present invention can maintain a high skin permeation rate (Flux value) with low variation over time after beginning of adhering, and can maintain the blood concentration stably for a long time, so that it is excellent in the point of compliance in the treatment of hypertension. In addition, the adhesive patch can be produced by a simple producing process in which two layers are formed separately by means of a usual solvent coating method and then laminated together as mentioned above, and further it has an excellent adhesivity and a low skin irritating property, and it shows no let-go and the like even after adhered for a long time and no skin irritation, so that it is useful as a transdermal patch.

EXAMPLES

In the following, the present invention is explained in more detail by way of examples. The invention, however, is not limited to these examples. Further, all "%" mean "% by mass" unless otherwise expressly stated.

Example 1

| [Drug reservoir layer] | |
|---|---|
| 2-Ethylhexyl acrylate/vinyl acetate/acrylic acid copolymer | 55% |
| Isopropyl myristate | 5% |
| Bisoprolol | 40% |
| [Skin adhesion layer] | |
| Styrene-isoprene-styrene block copolymer | 18% |
| Polyisobutylene (high molecular weight) | 6% |
| Polyisobutylene (low molecular weight) | 12% |
| Alicyclic saturated hydrocarbon resin | 42% |
| Liquid paraffin | 22% |

Bisoprolol and isopropyl myristate and a solution of 2-ethylhexyl acrylate/vinyl acetate/acrylic acid copolymer in heptane and ethyl acetate were mixed to obtain a coating solution. Then, the obtained coating solution was coated onto a release film made from polyethylene terephthalate, and thereafter the solvent was dried and removed to form an adhesive layer having a predetermined plaster body thickness (100 μm). Further, it was laminated together with a backing made from polyethylene terephthalate to obtain a drug reservoir layer of the present invention.

On the other hand, a coating solution of styrene-isoprene-styrene block copolymer, polyisobutylene (high molecular weight), polyisobutylene (low molecular weight), alicyclic saturated hydrocarbon resin and liquid paraffin in toluene was coated onto a release film made from polyethylene terephthalate, and thereafter the solvent was dried and removed to form a skin adhesion layer having a predetermined plaster body thickness (50 μm).

Finally, the release film made from polyethylene terephthalate was detached from the drug reservoir layer obtained earlier, adhesive layers were attached to each other to obtain the laminated transdermal patch of the present invention. Herein, the content of each constituent was as the above formulation.

Example 2

| [Drug reservoir layer] | |
|---|---|
| 2-Ethylhexyl acrylate/methyl acrylate/glycidyl methacrylate/acrylic acid copolymer | 60% |
| Isopropyl myristate | 5% |
| Bisoprolol | 35% |
| [Skin adhesion layer] | |
| Styrene-isoprene-styrene block copolymer | 19% |
| Polyisobutylene (high molecular weight) | 2.5% |
| Polyisobutylene (low molecular weight) | 5.5% |
| Alicyclic saturated hydrocarbon resin | 47% |
| Liquid paraffin | 26% |

Bisoprolol and isopropyl myristate and a solution or 2-ethylhexyl acrylate/methyl acrylate/glycidyl methacrylate/acrylic acid copolymer in ethyl acetate were mixed to obtain a coating solution. Then, the obtained coating solution was coated onto a release film made from polyethylene terephthalate, and thereafter the solvent was dried and removed to form an adhesive layer having a predetermined plaster body thickness (100 μm). Further, it was laminated together with a backing made from polyethylene terephthalate to obtain a drug reservoir layer of the present invention.

On the other hand, a coating solution of styrene-isoprene-styrene block copolymer, polyisobutylene (high molecular weight), polyisobutylene (low molecular weight), alicyclic saturated hydrocarbon resin and liquid paraffin in toluene was coated onto a release film made from polyethylene terephthalate, and thereafter the solvent was dried and removed to form a skin adhesion layer having a predetermined plaster body thickness (50 μm).

Finally, the release film made from polyethylene terephthalate was detached from the drug reservoir layer obtained earlier, adhesive layers were attached to each other to obtain the laminated transdermal patch of the present invention. Herein, the content of each constituent was as the above formulation.

Comparative Example 1

| 2-Ethylhexyl acrylate/vinyl acetate/acrylic acid copolymer | 55% |
|---|---|
| Isopropyl myristate | 5% |
| Bisoprolol | 40% |

Bisoprolol and isopropyl myristate and a solution of 2-ethylhexyl acrylate/vinyl acetate/acrylic acid copolymer in heptane and ethyl acetate were mixed to obtain a coating solution. Then, the obtained coating solution obtained was coated onto a release film made from polyethylene terephthalate, and thereafter the solvent was dried and removed to form an adhesive layer having a predetermined plaster body thickness (100 μm). Further, it was laminated together with a backing made from polyethylene terephthalate to obtain a transdermal patch.

Comparative Example 2

| [Drug reservoir layer] | |
|---|---|
| 2-Ethylhexyl acrylate/vinyl acetate/acrylic acid copolymer | 55% |
| Isopropyl myristate | 5% |
| Bisoprolol | 40% |
| [Skin adhesion layer] | |
| Polyisobutylene (high molecular weight) | 14% |
| Polyisobutylene (low molecular weight) | 81% |
| Liquid paraffin | 5% |

Bisoprolol and isopropyl myristate and a solution of 2-ethylhexyl acrylate/vinyl acetate/acrylic acid copolymer in heptane and ethyl acetate were mixed to obtain a coating solution. Then, the obtained coating solution was coated onto a release film made from polyethylene terephthalate, and thereafter the solvent was dried and removed to form an adhesive layer having a predetermined plaster body thickness (100 μm). Further, it was laminated together with a backing made from polyethylene terephthalate to obtain a drug reservoir layer.

On the other hand, a coating solution of polyisobutylene (high molecular weight), polyisobutylene (low molecular weight) and liquid paraffin in toluene was coated onto a release film made from polyethylene terephthalate, and thereafter the solvent was dried and removed to form a skin adhesion layer having a predetermined plaster body thickness (50 μm).

Finally, the release film made from polyethylene terephthalate was detached from the drug reservoir layer obtained earlier, adhesive layers were attached to each other to obtain the laminated transdermal patch. Herein, the content of each constituent was as the above formulation.

Comparative Example 3

| [Drug reservoir layer] | |
|---|---|
| 2-Ethylhexyl acrylate/vinyl acetate/acrylic acid copolymer | 55% |
| Isopropyl myristate | 5% |
| Bisoprolol | 40% |
| [Skin adhesion layer] | |
| 2-Ethylhexyl acrylate/vinyl acetate/acrylic acid copolymer | 100% |

Bisoprolol and isopropyl myristate and a solution of 2-ethylhexyl acrylate/vinyl acetate/acrylic acid copolymer in heptane and ethyl acetate were mixed to obtain a coating solution. Then, the obtained coating solution was coated onto a release film made from polyethylene terephthalate, and thereafter the solvent was dried and removed to form an adhesive layer having a predetermined plaster body thickness (100 μm). Further, it was laminated together with a backing made from polyethylene terephthalate to obtain a drug reservoir layer.

On the other hand, a coating solution of 2-ethylhexyl acrylate/vinyl acetate/acrylic acid copolymer in heptane and ethyl acetate was coated onto a release film made from polyethylene terephthalate, and thereafter the solvent was dried and removed to form a skin adhesion layer having a predetermined plaster body thickness (50 μm).

Finally, the release film made from polyethylene terephthalate was detached from the drug reservoir layer obtained earlier, and adhesive layers were attached to each other to obtain the laminated transdermal patch. Herein, the content of each constituent was as the above formulation.

Comparative Example 4

| [Drug reservoir layer] | |
|---|---|
| 2-Ethylhexyl acrylate/vinyl acetate/acrylic acid copolymer | 55% |
| Isopropyl myristate | 5% |
| Bisoprolol | 40% |
| [Skin adhesion layer] | |
| Silicone pressure-sensitive adhesive | 100% |

Bisoprolol and isopropyl myristate and a solution of 2-ethylhexyl acrylate/vinyl acetate/acrylic acid copolymer in heptane and ethyl acetate were mixed to obtain a coating solution. Then, the obtained coating solution was coated onto a release film made from polyethylene terephthalate, and thereafter the solvent was dried and removed to form an adhesive layer having a predetermined plaster body thickness (100 μm). Further, it was laminated together with a backing made from polyethylene terephthalate to obtain a drug reservoir layer.

On the other hand, a coating solution of silicone pressure-sensitive adhesive in heptane was coated onto a release film made from polyethylene terephthalate, and thereafter the solvent was dried and removed to form a skin adhesion layer having a predetermined plaster body thickness (50 μm).

Finally, the release film made from polyethylene terephthalate was detached from the drug reservoir layer obtained earlier, and adhesive layers were attached to each other to obtain the laminated transdermal patch. Herein, the content of each constituent was as the above formulation.

Examples 3 to 9

| [Drug reservoir layer] | |
|---|---|
| 2-Ethylhexyl acrylate/butyl acrylate/acrylic acid copolymer | 54.5% |
| Isopropyl myristate | 5.0% |
| Filler | 0.5% |
| Bisoprolol | 40.0% |
| [Skin adhesion layer] | |
| Styrene-isoprene-styrene block copolymer | See Table 1 |
| Polyisobutylene (high molecular weight) | See Table 1 |
| Polyisobutylene (low molecular weight) | See Table 1 |
| Alicyclic saturated hydrocarbon resin | 45% |
| Liquid paraffin | 25% |

TABLE 1

| Example | SIS/PIB ratio | SIS | PIB (high molecular weight) | PIB (low molecular weight) |
|---|---|---|---|---|
| 3 | 100/0 | 30.0% | 0.0% | 0.0% |
| 4 | 90/10 | 27.0% | 0.6% | 2.4% |

TABLE 1-continued

| Example | SIS/PIB ratio | SIS | PIB (high molecular weight) | PIB (low molecular weight) |
|---|---|---|---|---|
| 5 | 80/20 | 24.0% | 1.2% | 4.8% |
| 6 | 70/30 | 21.0% | 1.8% | 7.2% |
| 7 | 60/40 | 18.0% | 2.4% | 9.6% |
| 8 | 50/50 | 15.0% | 3.0% | 12.0% |
| 9 | 40/60 | 12.0% | 3.6% | 14.4% |

A dispersion wherein a filler is dispersed in 2-ethylhexyl acrylate/butyl acrylate/acrylic acid copolymer dissolved in ethyl acetate, toluene and hexane was mixed with bisoprolol and isopropyl myristate to obtain a coating solution. Then, the obtained coating solution was coated onto a release film made from polyethylene terephthalate, and thereafter the solvent was dried and removed to form an adhesive layer having a predetermined plaster body thickness (100 μm). Further, it was laminated together with a backing made from polyethylene terephthalate to obtain a drug reservoir layer of the present invention. Herein, the content of each constituent was as the above formulation.

On the other hand, a coating solution of styrene-isoprene-styrene block copolymer [SIS], polyisobutylene [PIB] (high molecular weight), polyisobutylene [PIB] (low molecular weight), alicyclic saturated hydrocarbon resin and liquid paraffin in toluene was coated onto a release film made from polyethylene terephthalate, and thereafter the solvent was dried and removed to form a skin adhesion layer having a predetermined plaster body thickness (50 μm). Herein, the content of each constituent was as the formulation shown in the above Table.

Finally, the release film made from polyethylene terephthalate was detached from the drug reservoir layer obtained earlier, and adhesive layers were attached to each other to obtain the laminated transdermal patch of the present invention (Examples 3 to 9).

Comparative Example 5

| [Drug reservoir layer] | |
|---|---|
| 2-Ethylhexyl acrylate/butyl acrylate/acrylic acid copolymer | 54.5% |
| Isopropyl myristate | 5.0% |
| Filler | 0.5% |
| Bisoprolol | 40.0% |
| [Skin adhesion layer] | |
| Polyisobutylene (high molecular weight) | 6.0% |
| Polyisobutylene (low molecular weight) | 24.0% |
| Alicyclic saturated hydrocarbon resin | 45% |
| Liquid paraffin | 25% |

A dispersion wherein a filler is dispersed in 2-ethylhexyl acrylate/butyl acrylate/acrylic acid copolymer dissolved in ethyl acetate, toluene and hexane was mixed with bisoprolol and isopropyl myristate to obtain a coating solution. Then, the obtained coating solution was coated onto a release film made from polyethylene terephthalate, and thereafter the solvent was dried and removed to form an adhesive layer having a predetermined plaster body thickness (100 μm). Further, it was laminated together with a backing made from polyethylene terephthalate to obtain a drug reservoir layer. Herein, the content of each constituent was as the above formulation.

On the other hand, a coating solution of styrene-isoprene-styrene block copolymer [SIS], polyisobutylene [PIB] (high molecular weight), polyisobutylene [PIB] (low molecular weight), alicyclic saturated hydrocarbon resin, and liquid paraffin in toluene was coated onto a release film made from polyethylene terephthalate, and thereafter the solvent was dried and removed to form a skin adhesion layer having a predetermined plaster body thickness (50 μm). Herein, the content of each constituent was as the formulation shown in the above Table.

Finally, the release film made from polyethylene terephthalate was detached from the drug reservoir layer obtained earlier, and adhesive layers were attached to each other to obtain the laminated transdermal patch.

Test 1: Hairless Mouse Skin Permeation Test

A skin (abdomen) which was excised from a hairless mouse of 7 to 10 weeks old and from which fats were removed was used. The patch obtained in Examples or Comparative examples (5 cm$^2$) was adhered on the stratum corneum side of the skin which was installed in a flow-through type diffusion cell, the dermal side being positioned to a receptor layer side. Then, pH 7.4 phosphate buffered physiological saline was used on the receptor side, and warm water was circulated around the outer part so that the temperature of the skin surface is 32±1° C. The flow rate was set at 7.5 mL/hour, and samplings were carried out at every 2 hours. As to the receptor solutions obtained at each point, the flow amounts were accurately measured, and the drug concentrations were measured by a high-performance liquid chromatography method, and the permeation rate per hour of each Example and Comparative example was calculated by measured values of the flow amount and the drug concentration.

Figure 1:
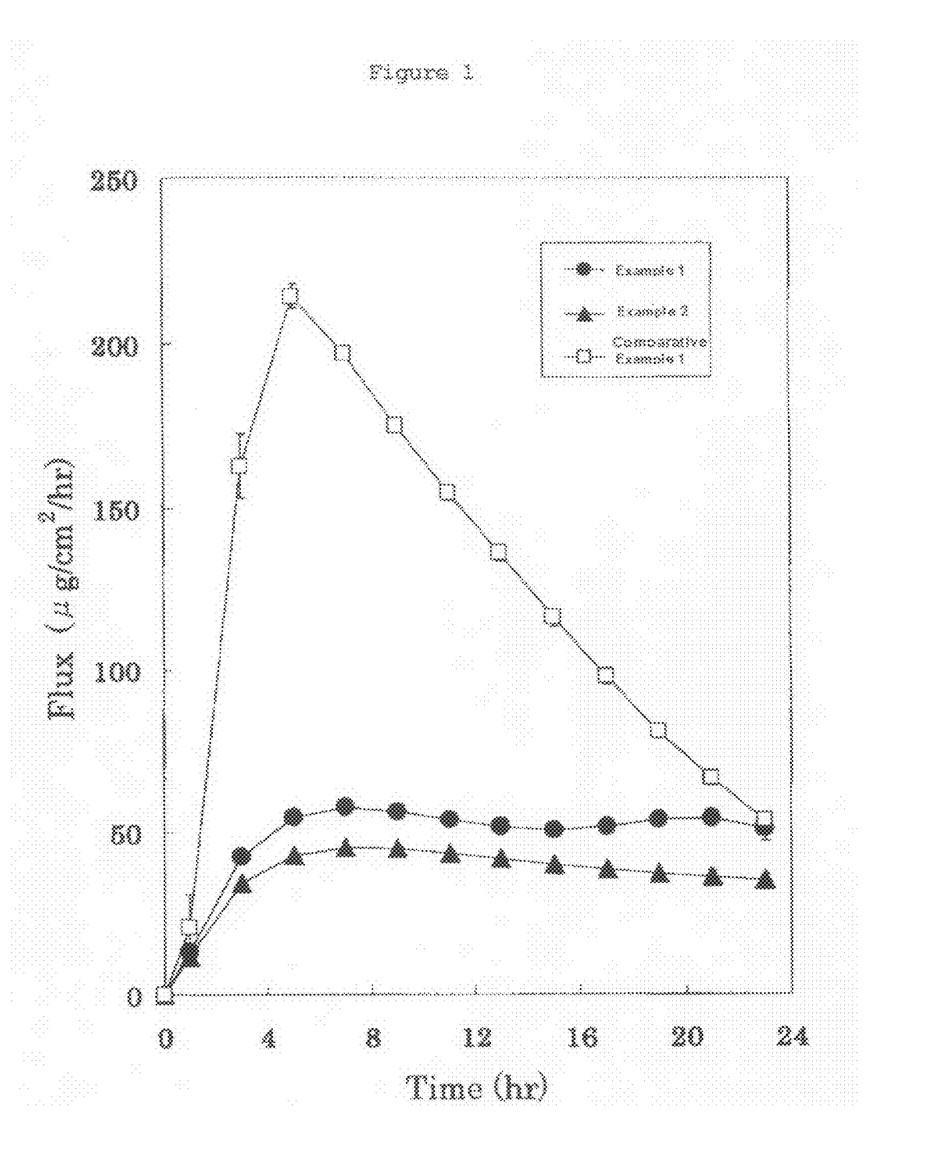
FIG. 1 shows the skin permeation rate of bisoprolol from each preparation.
Figure 2:
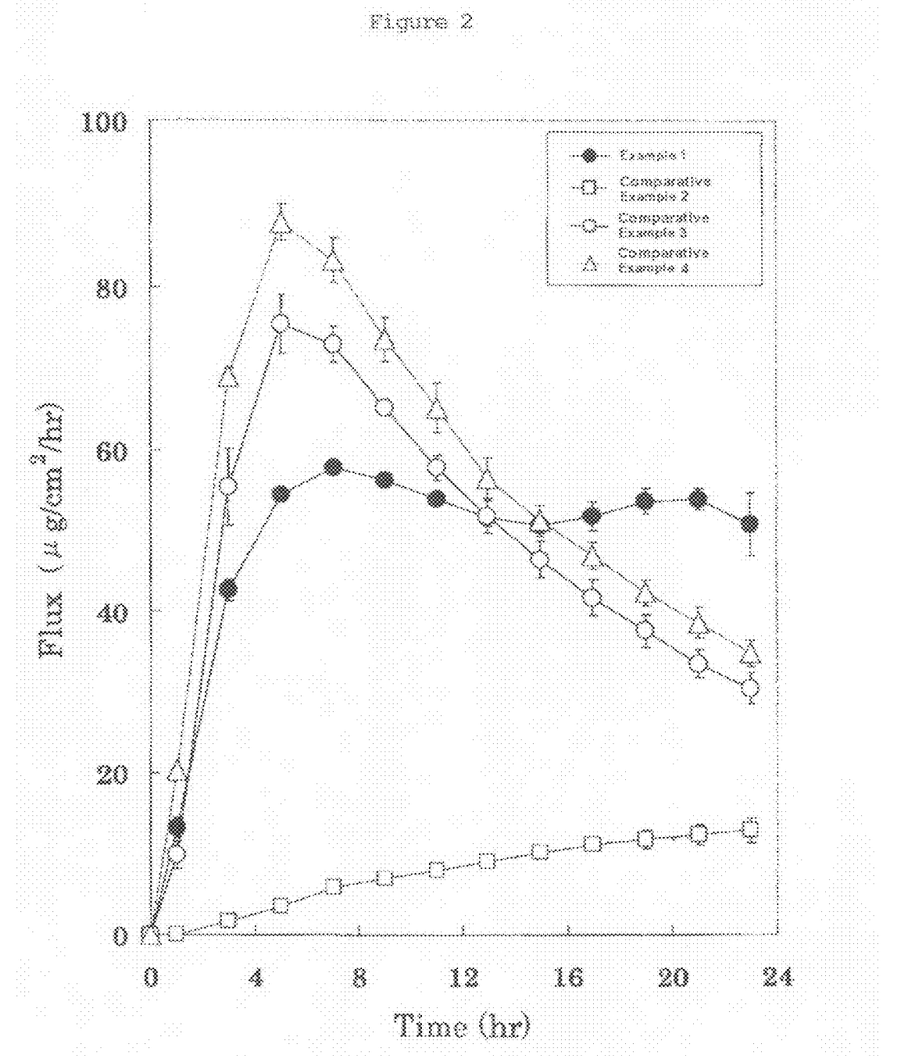
FIG. 2 shows the skin permeation rate of bisoprolol from each preparation.

As a result of the test, the preparations according to Examples 1 and 2 showed sufficient skin permeation rates and can maintain the skin permeation rates in a sustained manner (FIGS. 1 and 2).

The skin permeation rate of the preparation according to Comparative example 1 becomes transiently very high and then diminished, but it cannot sustainably maintain a stable skin permeation rate (FIG. 1).

The preparation according to Comparative example 2 cannot provide a sufficient skin permeation rate (FIG. 2).

The preparations according to Comparative examples 3 and 4 can provide sufficient skin permeation rates, but they cannot sustainably maintain stable skin permeation rates (FIG. 2).

Test 2: Adhesion Test

Adhesion of the obtained preparations was evaluated by a finger tack test based on the following criteria. The results are shown in Table 2.

TABLE 2

| | Physical property (adhesion) | Skin permeability | Skin permeation sustainability |
|---|---|---|---|
| Example 1 | ○ | ○ | ○ |
| Example 2 | ○ | ○ | ○ |
| Comparative example 1 | ⊚ | ⊚ | X |
| Comparative example 2 | X (Bleed) | X | X |
| Comparative example 3 | ○ | ○ | X |
| Comparative example 4 | X (Bleed) | ○ | X |

⊚: Very strong,
○: Strong (sufficient),
X: Weak (insufficient)

Test 3: Peel Test (180 Degree Peel Adhesion Test)

A test piece of width 1 cm×length 10 cm was taken from a sample, adhered on a cleaned bakelite test plate with the adhesion surface of the test piece oriented to lower side, and pressure-bonded by a roller applied from the top of the test piece. 30 Minutes after pressure-bonding, an end of the test piece was folded to 180 degree over about 1 cm, and the test piece was fixed to an upper chuck, and the test plate to a lower chuck, and peeling was performed with the speed of 300 mm/minute. The adhesivity at the time of peeling was recorded on a chart, and the part of 15% to 85% after the beginning of the recording was quartered, and the average value of five points including both ends were determined as the adhesivity. The test was conducted with three test pieces per lot. The results are shown in Table 3.

TABLE 3

|  | Skin permeability | | Physical property |
|---|---|---|---|
|  | SIS/PIB | Jmax (μg/cm²/h) | Sustainability | 180 Degree peel (gf/cm) |
| Example 3 | 100/0 | 77.5 | ○ | 9.98 |
| Example 4 | 90/10 | 73.1 | ○ | 15.28 |
| Example 5 | 80/20 | 69.5 | ○ | 16.51 |
| Example 6 | 70/30 | 61.3 | ○ | 29.74 |
| Example 7 | 60/40 | 55.3 | ○ | 90.54 |
| Example 8 | 50/50 | 51.3 | ○ | 93.00 |
| Example 9 | 40/60 | 48.2 | ○ | 316.25 |
| Comparative example 5 | 0/100 | — | — | Cohesion failure |

As shown in Table 3, no significant impact on skin permeability was observed even if SIS/PIB ratio was varied, and every preparation showed a moderate maximum skin permeation rate (Jmax) and a good sustainability. In addition, the adhesive properties varied depending on SIS/PIB ratio, and when the ratio was 70/30 to 40/60, it showed especially excellent adhesive properties.

As illustrated in the Examples, the transdermal patch of the present invention can be produced easily, can lead bisoprolol to be transdermally absorbed at a stable skin permeation rate for a long time in a sustained manner, and has an excellent adherence to skin, and is useful for the treatment of hypertension.

The invention claimed is:

1. A transdermal patch for sustained release at a constant concentration comprising a backing and a pressure-sensitive adhesive layer which comprises multiple layers, wherein the pressure-sensitive adhesive layer comprises (i) a drug reservoir layer containing a drug and an acrylic pressure-sensitive adhesive; and (ii) a skin adhesion layer containing a styrene-isoprene-styrene block copolymer on the skin contact side, the acrylic pressure-sensitive adhesive is a copolymer comprising (meth)acrylic acid having a carboxyl group as a monomer unit, and the drug is represented by the general formula (I)

[Chem. 1]

wherein
R is selected from the group consisting of 2-isopropoxyethoxymethyl, carbamoylmethyl, and 2-methoxyethyl groups, or a pharmaceutically acceptable salt thereof,
wherein the drug reservoir layer further comprises a solubilizer and/or a permeation enhancer,
wherein the skin adhesion layer is laminated on the drug reservoir layer,
wherein the transdermal patch provides sustained release of the drug at a constant release rate over 24 hours upon application.

2. The transdermal patch according to claim 1, wherein R is a 2-isopropoxyethoxymethyl group.

3. The transdermal patch according to claim 1, wherein the acrylic pressure-sensitive adhesive is a copolymer comprising 2-ethylhexyl acrylate as a monomer unit.

4. The transdermal patch according to claim 1, wherein the skin adhesion layer further comprises one or more selected from the group consisting of a synthetic rubber, a tackifier resin, and a plasticizer.

5. The transdermal patch according to claim 4, wherein the skin adhesion layer contains polyisobutylene as the synthetic rubber at 5 to 20% by mass based on the total amount of the compounds contained in the skin adhesion layer.

6. The transdermal patch according to claim 1, wherein the content of the drug is 10 to 60% by mass based on the total amount of compounds contained in the drug reservoir layer.

7. The transdermal patch according to claim 1, wherein the drug reservoir layer and comprises isopropyl myristate as the permeation enhancer.

8. The transdermal patch according to claim 6, wherein the drug reservoir layer contains isopropyl myristate as the permeation enhancer at 1 to 40% by mass based on the total amount of the compounds contained in the drug reservoir layer.

9. The transdermal patch according to claim 5, wherein two or more polyisobutylenes having different molecular weights are used in combination.

10. The transdermal patch according to claim 8, wherein the skin adhesion layer contains polyisobutylene as the synthetic rubber at 5 to 20% by mass based on the total amount of compounds contained in the skin adhesion layer and two or more polyisobutylenes having different molecular weights are used in combination.

* * * * *

UNITED STATES PATENT AND TRADEMARK OFFICE
CERTIFICATE OF CORRECTION

PATENT NO.         : 8,524,273 B2                                    Page 1 of 1
APPLICATION NO.    : 12/224586
DATED              : September 3, 2013
INVENTOR(S)        : Satoshi Amano et al.

It is certified that error appears in the above-identified patent and that said Letters Patent is hereby corrected as shown below:

In the Claims

At column 15, claim number 1, line number 56, please change the letter (I) to the arabic numeral (1)

At column 16, claim number 1, line number 18, please add the word "and" to "reservoir layer, and"

At column 16, claim number 7, line number 39, please remove the word "and" between the words "layer and comprises"

Signed and Sealed this
Twenty-sixth Day of August, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,524,273 B2
APPLICATION NO. : 12/224586
DATED : September 3, 2013
INVENTOR(S) : Amano et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1035 days.

Signed and Sealed this
Twentieth Day of October, 2015

Michelle K. Lee
*Director of the United States Patent and Trademark Office*

UNITED STATES PATENT AND TRADEMARK OFFICE
CERTIFICATE OF CORRECTION

PATENT NO. : 8,524,273 B2
APPLICATION NO. : 12/224586
DATED : September 3, 2013
INVENTOR(S) : Satoshi Amano et al.

It is certified that error appears in the above-identified patent and that said Letters Patent is hereby corrected as shown below:

In the Claims

At Column 16, Claim number 7, Line number 38, please renumber Claim 7 to properly be Claim 2, and move this Claim to immediately follow Claim 1 (at Column 16, Line number 21).

At Column 16, Claim number 2, Line number 22, please renumber Claim 2 to properly be Claim 3.

At Column 16, Claim number 2, Line number 22, please remove the number "1" and add the number "2".

At Column 16, Claim number 3, Line number 24, please renumber Claim 3 to properly be Claim 4.

At Column 16, Claim number 3, Line number 24, please remove the number "1" and add the number "2".

At Column 16, Claim number 4, Line number 27, please renumber Claim 4 to properly be Claim 5.

At Column 16, Claim number 4, Line number 27, please remove the number "1" and add the number "2".

At Column 16, Claim number 5, Line number 31, please renumber Claim 5 to properly be Claim 6.

At Column 16, Claim number 5, Line number 31, please remove the number "4" and add the number "5".

At Column 16, Claim number 6, Line number 35, please renumber Claim 6 to properly be Claim 7.

At Column 16, Claim number 6, Line number 35, please remove the number "1" and add the number "2".

Signed and Sealed this
Eleventh Day of April, 2017

Michelle K. Lee
*Director of the United States Patent and Trademark Office*

CERTIFICATE OF CORRECTION (continued)
U.S. Pat. No. 8,524,273 B2

At Column 16, Claim number 8, Line number 41, please remove the number "6" and add the number "7".

At Column 16, Claim number 9, Line number 46, please remove the number "5" and add the number "6".